US010342995B2

(12) United States Patent
Bach

(10) Patent No.: US 10,342,995 B2
(45) Date of Patent: *Jul. 9, 2019

(54) SYSTEM AND METHOD FOR SCANNED ION BEAM INTERPLAY EFFECT MITIGATION USING RANDOM REPAINTING

(71) Applicant: Varian Medical Systems Particle Therapy GmbH, Troisdorf (DE)

(72) Inventor: Markus Bach, Overath (DE)

(73) Assignee: VARIAN MEDICAL SYSTEMS PARTICLE THERAPY GMBH., Troisdorf (DE)

(*) Notice: Subject to any disclaimer, the term of this patent is extended or adjusted under 35 U.S.C. 154(b) by 0 days.

This patent is subject to a terminal disclaimer.

(21) Appl. No.: 15/988,750

(22) Filed: May 24, 2018

(65) Prior Publication Data

US 2018/0272154 A1  Sep. 27, 2018

Related U.S. Application Data

(63) Continuation of application No. 15/282,884, filed on Sep. 30, 2016, now Pat. No. 9,981,144.

(51) Int. Cl.
*A61N 5/10* (2006.01)

(52) U.S. Cl.
CPC .......... *A61N 5/1067* (2013.01); *A61N 5/103* (2013.01); *A61N 5/1044* (2013.01); *A61N 5/1049* (2013.01); *A61N 5/1081* (2013.01); *A61N 2005/1087* (2013.01)

(58) Field of Classification Search
CPC ...... A61N 5/10; A61N 5/1048; A61N 5/1064; A61N 5/1065; A61N 5/1067; A61N 5/1072

USPC ............................................ 250/492.1, 492.3
See application file for complete search history.

(56) References Cited

U.S. PATENT DOCUMENTS

| | | |
|---|---|---|
| 4,958,078 A | 9/1990 | Becchetti |
| 5,866,912 A | 2/1999 | Slater et al. |
| 8,632,448 B1 | 1/2014 | Schulte et al. |
| 8,963,108 B2 | 2/2015 | Matteo et al. |
| 9,084,887 B2 | 7/2015 | Schulte et al. |
| 9,981,144 B2 * | 5/2018 | Bach .................... A61N 5/1067 |
| 2007/0201613 A1 * | 8/2007 | Lu ........................ A61N 5/1049 378/65 |
| 2008/0191142 A1 | 8/2008 | Pedroni |
| 2009/0189095 A1 * | 7/2009 | Flynn ...................... A61N 5/10 250/492.3 |
| 2010/0243911 A1 | 9/2010 | Fujiii et al. |

(Continued)

FOREIGN PATENT DOCUMENTS

WO   WO2014155232 A1   10/2014

*Primary Examiner* — Jason L McCormack

(57) ABSTRACT

Interference of dose application in scanned ion beam therapy and organ motion, also called interplay effect, may lead to dose deviations at target volumes. Current repainting methods are susceptible to artifacts due to a predominant scanning direction, ranging from fringed field edges to under and overdosed regions (hot and cold spots). To overcome the difficulties inherent in the repainting techniques of conventional proton therapy systems, new random repainting techniques are described herein for mitigating the under-dose and/or over-dose pattern inherent in existing repainting techniques using a random repainting approach that randomly selects spot locations within the target area.

20 Claims, 10 Drawing Sheets

(56) References Cited

U.S. PATENT DOCUMENTS

| | | |
|---|---|---|
| 2010/0243921 A1 | 9/2010 | Flynn et al. |
| 2010/0301235 A1 | 12/2010 | Bert et al. |
| 2011/0101235 A1 | 5/2011 | Iwata |
| 2012/0119115 A1 | 5/2012 | Iwata |
| 2014/0121442 A1 | 5/2014 | Matteo et al. |
| 2015/0087887 A1 | 3/2015 | Seibert et al. |
| 2015/0099917 A1 | 4/2015 | Bula et al. |
| 2016/0016010 A1 | 1/2016 | Schulte et al. |

* cited by examiner

SYSTEM AND METHOD FOR SCANNED ION BEAM INTERPLAY EFFECT MITIGATION USING RANDOM REPAINTING

CROSS-REFERENCE TO RELATED APPLICATIONS

This application is a continuation of U.S. patent application Ser. No. 15/282,884, now U.S. Pat. No. 9,981,144, filed Sep. 30, 2016, which is incorporated herein by reference in its entirety.

This patent application is related to and incorporates by reference herein in their entirety, the following patent applications:
(1) U.S. patent application Ser. No. 15/087,292, entitled Automatic "Adaptive Pencil Beam Scanning" by Wulff et al., with filing date of Mar. 31, 2016; and
(2) U.S. patent application Ser. No. 15/087,800, entitled Automatic "System and Method for In-Layer Synchronization for Fast Spot Rescanning" by Bach et al., with filing date of Mar. 31, 2016.

TECHNICAL FIELD

Embodiments of this invention relate generally to directed irradiated particle beam applications. More specifically, embodiments of this invention are directed to improved methods and systems for directing a beam of irradiated particles to achieve a target dosage using a random repainting technique.

BACKGROUND OF THE INVENTION

Particle therapy is a type of external beam radiotherapy that generates beams of energetic protons, neutrons, or ions used for cancer treatment. Particle therapy works by providing energetic ionizing particles to target tissue (e.g., a tumor). These particles are used to destroy or damage the DNA of tissue cells.

Ion therapy is a type of external beam radiation therapy that is characterized by the use of a beam of ions to irradiate diseased tissue. A chief advantage of ion therapy over other conventional therapies such as X-ray or neutron radiation therapies is that ion radiation has the ability to stop in matter—treatment dosages are applied as a sequence of proton beams with several energies three-dimensionally. The dose deposition of each monoenergetic, thin ("pencil") beam in a medium is characterized by a sharp increase in dose deposition (Single Bragg Peak) directly before the end of the beam depth, thereby limiting the inadvertent exposure of non-target cells to potentially harmful radiation.

The pencil beam scanning technique allows the deflection of monoenergetic beams to prescribed voxels (in transversal direction/x- and y-coordinates for associated beam depths) in medium—the so called spot scanning technique (e.g., a "raster scan" of applications). Prescribed spot positions for a scanned ion beam delivery are typically arranged on a fixed (raster) pattern for each energy and therefore deliverable on a fixed scanning path within an energy layer (for example on a meander like path). By superposition of several ion beams of different energies, a Bragg peak can be spread out to cover target volumes by a uniform, prescribed dose. This enables ion therapy treatments to more precisely localize the radiation dosage relative to other types of external beam radiotherapy. During ion therapy treatment, a particle accelerator such as a cyclotron or synchrotron is used to generate a beam of ions from, for example, an internal ion source located in the center of the cyclotron. The ions in the beam are accelerated (via a generated electric field), and the beam of accelerated ions is subsequently "extracted" and magnetically directed through a series of interconnecting tubes (called a beamline), often through multiple chambers, rooms, or even floors of a building, before finally being applied through an end section of beam line (called Nozzle) to a target volume in a treatment room.

As the volumes (e.g., organs, or regions of a body) targeted for radiation therapy are often below the surface of the skin and/or extend in three dimensions, and since ion therapy—like all radiation therapies—can be harmful to intervening tissue located in a subject between the target area and the beam emitter, the precise calculation and application of correct dosage amounts and positions are critical to avoid exposing non target areas to the radiation beyond what is necessary. However, the effective ion range is variable based on a number of uncertainties, such as positional discrepancies and motion, and understanding of the sources and magnitude of these uncertainties is key for producing treatment plans which are robust and can withstand these uncertainties. Furthermore, for intensity-modulated particle therapy (IMPT), steep dose gradients are often used at the target border and field edges to enhance dose conformity. This increases the complexity of fluence maps and decreases robustness to uncertainties.

To address these issues, adaptive therapy techniques have been proposed that incorporate such uncertainties directly into the optimization algorithm. According to some techniques, robustness may be included in a multi-criteria optimization framework, allowing a multi-objective optimization function to balance robustness and conformity. For mitigating the effects of motion specifically, rescanning ("repainting") techniques have been developed to deliver the prescribed dose distribution to each layer of the target volume. However, the repainting techniques currently employed lead to an under-dose and/or over-dose pattern based on motion parameters (e.g., initial phase, period, amplitude) and the speed and/or direction of the scanning, leading to artifacts caused by a predominant scanning direction. What is needed is an approach to repainting that mitigates the under-dose and/or over-dose pattern inherent in existing repainting techniques while achieving a relatively uniform dose distribution.

SUMMARY

This Summary is provided to introduce a selection of concepts in a simplified form that is further described below in the Detailed Description. This Summary is not intended to identify key features or essential features of the claimed subject matter, nor is it intended to be used to limit the scope of the claimed subject matter.

To overcome the difficulties inherent in the repainting techniques of conventional proton therapy systems, such as effects caused by scanning direction and speed, new random repainting techniques are described herein for mitigating the under-dose and/or over-dose pattern inherent in existing repainting techniques. According to one embodiment, a method for irradiating a target area using randomly distributed spot locations is disclosed. The method includes accessing a target radiation plan, the target radiation plan including a temporal and spatial sequence for administering a target dosage to a target area using a plurality of applications of a directed beam of protons, monitoring a movement of the target area, adjusting the target radiation plan to align the plurality of applications of the directed beam of protons with a movement of the target area to generate an adjusted target radiation plan, applying a directed beam of protons to a first set of spot locations of the target area according to the adjusted target radiation plan, where the first set of spot locations is selected at random, and applying the directed beam of protons to a second set of spot locations of the target area according to the adjusted target radiation plan, where the second set of spot locations is selected at random.

According to another embodiment, a radiation application system is disclosed. The radiation application system includes a particle accelerator configured to produce a plurality of irradiated particles, a gantry configured to receive the plurality of irradiated particles and to rotate around a target subject, a treatment nozzle included in the gantry, the treatment nozzle configured to emit the plurality of irradiated particles as a directed beam at a target area in the target subject, a sensor device configured to monitor a movement of the target area, and a client computing device. The client computing device includes a memory device configured to store a target radiation plan including a timed sequence for administering a target dosage to the target area using a plurality of applications of the directed beam of irradiated particles, where the plurality of applications include a plurality of spot locations selected at random, and a processor configured adjust the target radiation plan to align the plurality of applications of the directed beam of protons with a movement of the target area, and to program a movement of the gantry around the target subject and an emission of the treatment nozzle to apply the directed beam of irradiated particles at the plurality of spot locations selected at random for the target area according to the adjusted target radiation plan.

According to another embodiment, a non-transitory computer readable medium having a plurality of programmed instructions which, when executed by a processor in a computing system, is operable to implement a target radiation plan using randomly distributed spot locations. The a non-transitory computer readable medium includes instructions to access a target radiation plan, the target radiation plan including a timed sequence for administering a target dosage to a target area using a plurality of applications of a spot-scanning beam of protons, instructions to monitor a periodic movement of the target area, instructions to generate an adjusted target radiation plan by adjusting the target radiation plan align the plurality of applications of the directed beam of protons with a movement of the target area, instructions to apply a directed beam of protons to a first set of spot locations of the target area according to the adjusted target radiation plan, where the first set of spot locations are selected at random, and instructions to apply the directed beam of protons to a second set of spot locations of the target area according to the adjusted target radiation plan, where the second set of spot locations are selected at random.

BRIEF DESCRIPTION OF DRAWINGS

The accompanying drawings, which are incorporated in and form a part of this specification, illustrate embodiments of the disclosure and, together with the description, serve to explain the principles of the presently claimed subject matter.

DETAILED DESCRIPTION

Figure 1:
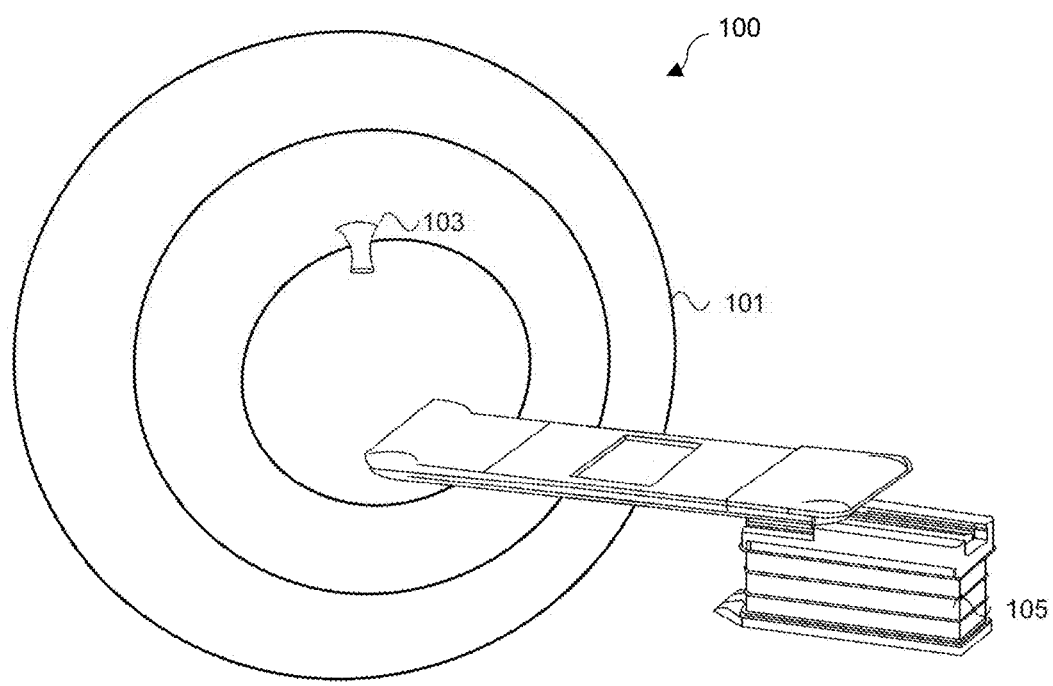
FIG. 1 depicts an exemplary proton therapy device in accordance with embodiments of the present invention.

Reference will now be made in detail to several embodiments. While the subject matter will be described in conjunction with the alternative embodiments, it will be understood that they are not intended to limit the claimed subject matter to these embodiments. On the contrary, the claimed subject matter is intended to cover alternative, modifications, and equivalents, which may be included within the spirit and scope of the claimed subject matter as defined by the appended claims.

Furthermore, in the following detailed description, numerous specific details are set forth in order to provide a thorough understanding of the claimed subject matter. However, it will be recognized by one skilled in the art that embodiments may be practiced without these specific details or with equivalents thereof. In other instances, well-known processes, procedures, components, and circuits have not been described in detail as not to unnecessarily obscure aspects and features of the subject matter.

Portions of the detailed description that follow are presented and discussed in terms of a process. Although operations and sequencing thereof are disclosed in a figure herein (e.g., FIG. 7) describing the operations of this process, such operations and sequencing are exemplary. Embodiments are well suited to performing various other operations or variations of the operations recited in the flowchart of the figure herein, and in a sequence other than that depicted and described herein.

Some portions of the detailed description are presented in terms of procedures, operations, logic blocks, processing, and other symbolic representations of operations on data bits that can be performed on computer memory. These descriptions and representations are the means used by those skilled in the data processing arts to most effectively convey the substance of their work to others skilled in the art. A procedure, computer-executed operation, logic block, process, etc., is here, and generally, conceived to be a self-consistent sequence of operations or instructions leading to a desired result. The operations are those requiring physical manipulations of physical quantities. Usually, though not necessarily, these quantities take the form of electrical or magnetic signals capable of being stored, transferred, combined, compared, and otherwise manipulated in a computer system. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise as apparent from the following discussions, it is appreciated that throughout, discussions utilizing terms such as "accessing," "writing," "including," "storing," "transmitting," "traversing," "associating," "identifying" or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

It is appreciated that throughout, discussions utilization of the term "painting", "repainting", "scanning", or "rescanning" shall refer to irradiating a target area with a proton beam.

While the following example configurations are shown as incorporating specific, enumerated features and elements, it is understood that such depiction is exemplary. Accordingly, embodiments are well suited to applications involving different, additional, or fewer elements, features, or arrangements.

Random Repainting for Scanned Ion Beam Interplay Effect Mitigation

The claimed subject matter is directed to a particle beam control system. To overcome the difficulties inherent in the repainting techniques of conventional proton therapy systems, new random repainting techniques are described herein for mitigating the under-dose and/or over-dose pattern inherent in existing repainting techniques. According to one embodiment, a method for irradiating a target area using randomly distributed spot locations is disclosed. The method includes accessing a target radiation plan, the target radiation plan including a temporal and spatial sequence for administering a target dosage to a target area using a plurality of applications of a directed beam of protons, monitoring a movement of the target area, adjusting the target radiation plan to align the plurality of applications of the directed beam of protons with a movement of the target area to generate an adjusted target radiation plan, applying a directed beam of protons to a first set of spot locations of the target area according to the adjusted target radiation plan, where the first set of spot locations is selected at random, and applying the directed beam of protons to a second set of spot locations of the target area according to the adjusted target radiation plan, where the second set of spot locations is selected at random.

According to another embodiment, a radiation application system is disclosed. The radiation application system includes a particle accelerator configured to produce a plurality of irradiated particles, a gantry configured to receive the plurality of irradiated particles and to rotate around a target subject, a treatment nozzle included in the gantry, the treatment nozzle configured to emit the plurality of irradiated particles as a directed beam at a target area in the target subject, a sensor device configured to monitor a movement of the target area, and a client computing device. The client computing device includes a memory device configured to store a target radiation plan including a timed sequence for administering a target dosage to the target area using a plurality of applications of the directed beam of irradiated particles, where the plurality of applications include a plurality of spot locations selected at random, and a processor configured adjust the target radiation plan to align the plurality of applications of the directed beam of protons with a movement of the target area, and to program a movement of the gantry around the target subject and an emission of the treatment nozzle to apply the directed beam of irradiated particles at the plurality of spot locations selected at random for the target area according to the adjusted target radiation plan.

According to another embodiment, a non-transitory computer readable medium having a plurality of programmed instructions which, when executed by a processor in a computing system, is operable to implement a target radiation plan using randomly distributed spot locations. The a non-transitory computer readable medium includes instructions to access a target radiation plan, the target radiation plan including a timed sequence for administering a target dosage to a target area using a plurality of applications of a spot-scanning beam of protons, instructions to monitor a periodic movement of the target area, instructions to generate an adjusted target radiation plan by adjusting the target radiation plan align the plurality of applications of the directed beam of protons with a movement of the target area, instructions to apply a directed beam of protons to a first set of spot locations of the target area according to the adjusted target radiation plan, where the first set of spot locations are selected at random, and instructions to apply the directed beam of protons to a second set of spot locations of the target area according to the adjusted target radiation plan, where the second set of spot locations are selected at random.

Exemplary Radiation Therapy Device

FIG. 1 depicts an exemplary radiation therapy device 100 in a treatment therapy room, in accordance with various embodiments of the claimed subject matter. As presented in FIG. 1, radiation therapy device 100 includes a gantry 101, a radiation treatment nozzle 103, and a subject positioner 105. In one or more embodiments, the gantry 101 may comprise an opening through which at least a portion of the subject positioner 105 is able to enter (e.g., via automatic and/or mechanical means). In one or more embodiments, at least a portion of the gantry may be operable to rotate around the opening (typically while at least a portion of the subject positioner is disposed within). For example, as depicted in FIG. 1, the gantry 101 may be implemented as a ring, at least a portion of which may be rotatable around an axis bisected by the subject positioner 105.

According to one or more embodiments, the gantry 101 is configured to receive irradiated particles through a beam line connected to a particle accelerator (not shown). The particle accelerator may be implemented as, but is not limited to, a proton accelerator such as a cyclotron or synchrotron. In one or more embodiments, the particle accelerator may be positioned remotely with respect to the treatment therapy room and may be shared between multiple radiation therapy devices housed in multiple treatment therapy rooms. Beam lines (e.g., vacuum sealed tubes or pipes used to transfer irradiated particles) are used to connect the particle accelerator to each of the radiation therapy devices. The irradiated particles are emitted from the radiation therapy device 100 through the treatment nozzle 103 located on the gantry 101. In one or more embodiments, the treatment nozzle 103 is rotated about the opening of the gantry 101 through a rotation of at least a portion of the gantry. In alternate embodiments, movement of the treatment nozzle 103 may be performed via movement of one or more robotic appendages coupled to the gantry 101.

In one or more embodiments, the subject positioner 105 may include a support structure (such as a table, chair, bench, or bed) upon which a treatment subject may lie, sit, or rest upon. According to further embodiments, portions of the subject positioner 105 may be capable of movement, via automatic and/or mechanical means. For example, the incline of a portion of the resting surface may be increased or decreased (e.g., physically via a mechanism or automatically through a graphical user interface). Portions of the subject positioner 105 may also be equipped with means to rotate, extend, or retract. For example, according to one or more embodiments, a portion of the resting surface of the subject positioner 105 may be extended or physically positioned into an opening of the gantry 101, such that a treatment subject resting on the subject positioner 105 bisects the plane at which the treatment nozzle 103 is directed.

One or both of the gantry 101 and the subject positioner 105 is/are capable of maneuvering, either independently or in conjunction, to align a treatment subject positioned on the subject positioner 105 with a treatment nozzle 103. Movement of the gantry 101 and/or subject positioner 105 may include, but is not limited to, rotation, extension, retraction, contraction, adduction, abduction, etc. of one or more articulated surfaces or portions of the gantry 101, and/or subject positioner 105. In one or more embodiments, treatment nozzle 103 may also be capable of limited movement, via multi-axial rotation, for example. Movement of the gantry 101, treatment nozzle 103, and/or subject positioner 105 may be performed automatically, via pre-programmed instructions that correspond to optimized alignments for desired iso-centers, or may be controlled remotely via a user interface.

A treatment subject may be positioned (e.g., by lying prone) on a subject positioner 105 at an initial or starting position. One or more portions of the subject positioner 105 may extend towards an opening presented by the gantry 101, such that a target region of the treatment subject is aligned with a position of the treatment nozzle 103, located on or around an inner surface of the gantry 101. In alternate or further embodiments, the gantry 101 may also rotate in an arc around the circumference of the gantry 101 to position the treatment nozzle 103 to produce the desired beam field or to do position verification of a treatment subject positioned on a subject positioner 105. Once the gantry 101, treatment nozzle 103, and/or subject positioner 105 are aligned in the desired orientation, treatment therapy may begin. Specifically, an iso-center in the treatment subject may be aligned with the treatment nozzle 103 via movement of the gantry 101 and/or subject positioner 105. In one or more embodiments, treatment therapy may comprise the application of irradiated particles generated at a (remote) particle accelerator, received in the gantry 101, and emitted (e.g., as a raster scan) in a beam field from the treatment nozzle 103 at an iso-center located in a treatment subject according to a pre-determined treatment therapy plan.

The treatment nozzle 103 may be configured to emit the irradiated particles in a spot scanning beam (also referred to as a "pencil beam"). Adjusting the energy level of the beam allows control of the depth at which the Bragg Peaks of the accelerated protons are located. The increased flexibility made available through three-dimensional spot scanning greatly improves the precision of the dose delivered to a patient so as to maximize dose delivery to a tumor and minimize damage to healthy tissue.

A spot-scanning beam may be produced by crossing two or more extracted beams at an extremely fine point in the radiation device. A target area (beam field) may be irradiated with a raster scan (two-dimensional emission) of the resultant spot scanning beam. In one or more embodiments, multiple beam fields sharing the same or proximate iso-centers may be irradiated with the spot scanning beam in a contiguous session, uninterrupted by application of the spot scanning beam to more distant or unrelated beam fields, for example. In further embodiments, beam fields that do not require the addition and/or removal of additional accessories such as (but not limited to) collimators, jaws, and range shifters, etc., may be irradiated in a contiguous beam application, as an automated treatment of a set of fields.

In one or more embodiments, a subject resting or positioned on the subject positioner may be monitored. For example, the motion of a target area within the subject may be monitored by, but is not limited to, continuous imaging the target volume and/or tracking one or more motion surrogates directly correlated to the motion and/or position of a target volume (not shown). These surrogates may include, for example, respiratory markers or ECG signals. Other methods for monitoring a target area may include, but are not limited to, implanted sensors, real-time imaging devices, or any other device suitable to monitor organ motion and/or the respiratory or cardiac cycle(s) of a subject. Monitoring of a target area may include measuring a frequency and duration of each phase or cycle of a periodic motion exhibited by the target area (e.g., displacement from a resting or default position) and the timing (e.g., duration) of transitions between phases. Monitoring of a target area may also include measuring the direction and the peak displacement from the resting or default position, mapped to phases of the periodic motion.

The monitored motion may be analyzed and the analyzed motion characteristics may be used, but are not limited, to adjust the timing, direction and sequence of directed particle beam radiation associated with prescribed radiation plans to better align beam applications to account for the motion exhibited by the target area. In one or more embodiments, the radiation plan may be stored with other radiation plans as a plurality of programmed instructions in a memory device of a controller (e.g., a computing device executing an application) of the radiation therapy device 100 and the emission of the beam of irradiated particles.

Random Repainting Results

A simulation tool based on treatment logs and motion information was developed to compare measurement results to expected dose distributions. Efficiency of repainting was analyzed by comparison to the static case. Quantitative analysis was performed with PTW VeriSoft 6.2. Simulations using mono-energetic plans with a 10×10 $cm^2$ scanning field size calculated by the Eclipse 13 treatment planning system demonstrate exemplary random repainting realized by randomly distributing single spot locations. Measurements were performed using an IAS, a two-dimensional amorphous silicon detector (relative dose measurements in air at isocenter) and a PTW 729XDR (absolute dose measurements with slabs of phantom material in front of the detector), both mounted to a motion platform (CIRS dynamic platform). Motion was considered with different cycles, directions and translations up to ±8 mm. Measurements were performed for a static case as reference, conventional repainting (repeated meander-like path), and random repainting.

Figure 2:
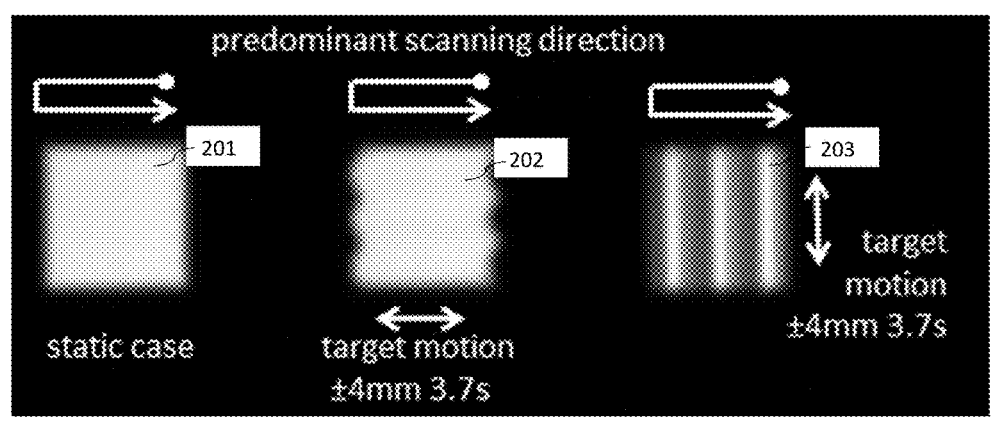
FIG. 2 depicts exemplary interplay effect for parallel scanning and perpendicular scanning of an organ in motion compared to a static case.

Interference of dose application in scanned ion beam therapy and organ motion, also called interplay effect, may lead to dose deviations at target volumes. Current repainting methods are susceptible to artifacts due to a predominant scanning direction, ranging from fringed field edges to under-dosed and over-dosed regions (hot and cold spots). With regard to FIG. 2, interplay effects for parallel scanning 202 and perpendicular scanning 203 with organ motions of 4 mm and 3.7 s are compared to a static case 201. For moving objects, the predominant scanning direction of the ion beam (e.g., proton beam) may interfere with the inner body motion of the target (interplay effect), resulting in a distorted dose distribution. Additional target margins will not mitigate the interplay effect if scanning and organ motions are perpendicular to each other causing to hot and cold regions to develop.

Figure 3:
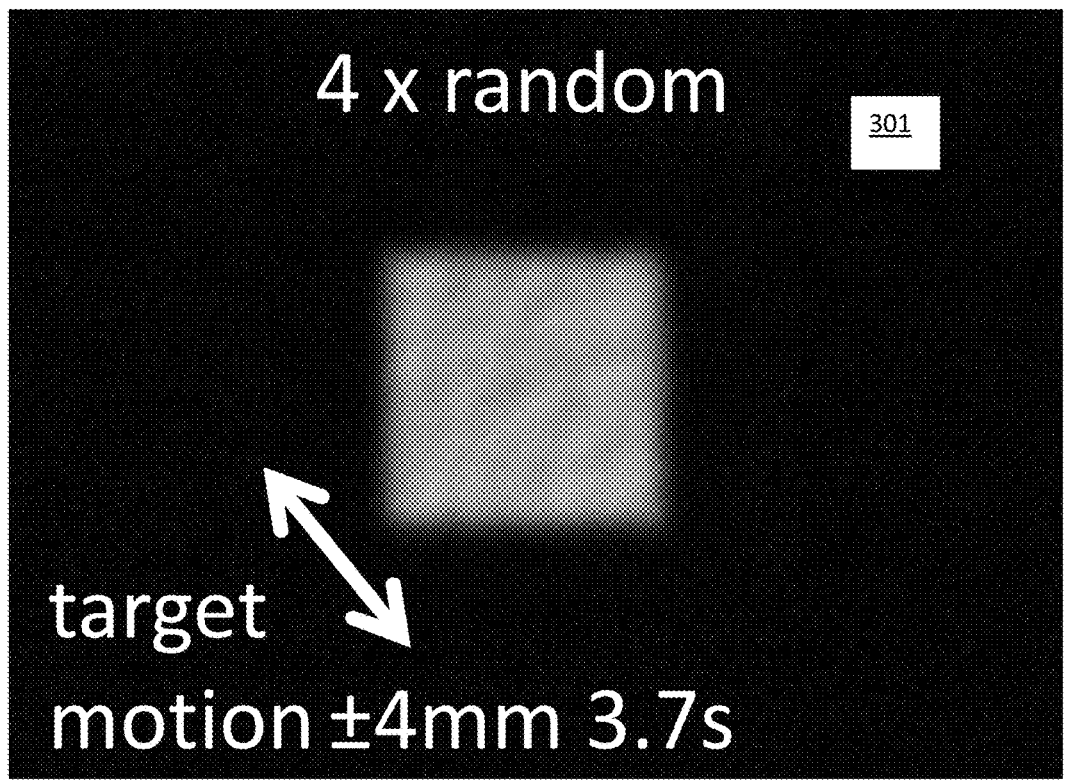
FIG. 3 depicts an exemplary motion cycle of a 4× random repainting application according to embodiments of the present invention.

With regard to FIG. 3, an exemplary motion cycle of a 4× random repainting application 301 is depicted according to embodiments of the present invention. A setup with parallel and orthogonal motion was chosen to contribute both types of artifacts. Summing up individual spot doses during a single random repaint demonstrates the mitigation of described interplay effects, where repainting techniques are used to blur or smear the interplay effects. Embodiments of the present invention repaint more effectively by randomizing the repainting spot pattern as depicted in FIG. 3 such that the irradiation has no predominant direction. These techniques yield considerable improvements in dose conformity for randomly repainting a single layer, thereby superseding motion path considerations for target and scanning order to prevent hot and cold spots during treatment planning. When applied to multiple layers, these techniques may reduce target margins and the number of repaints (rescans) necessary to achieve a target dose compared to conventional approaches. High resolution measurements of four random repaints with oblique target motion of ±4 mm reveals a moderate deviation from the reference case 201. The increased overall scanning travel distance leads to a prolonged irradiation time (e.g., 20.2 s or higher) compared to 17.4 s for the conventional approach with the same number of repaints and 10.7 s without repainting.

Figure 4A:
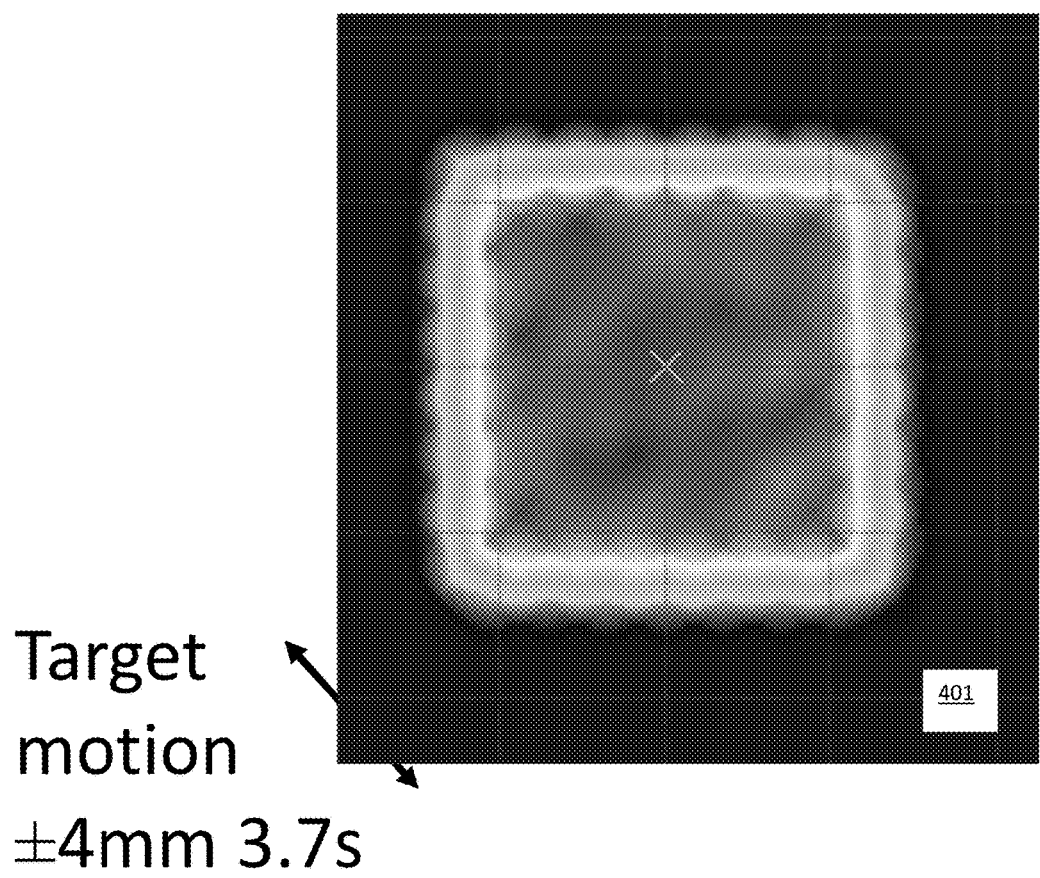
FIG. 4A illustrates an absolute dose measurement of an exemplary 4× random repainting application for a target in motion according to embodiments of the present invention.
Figure 4B:
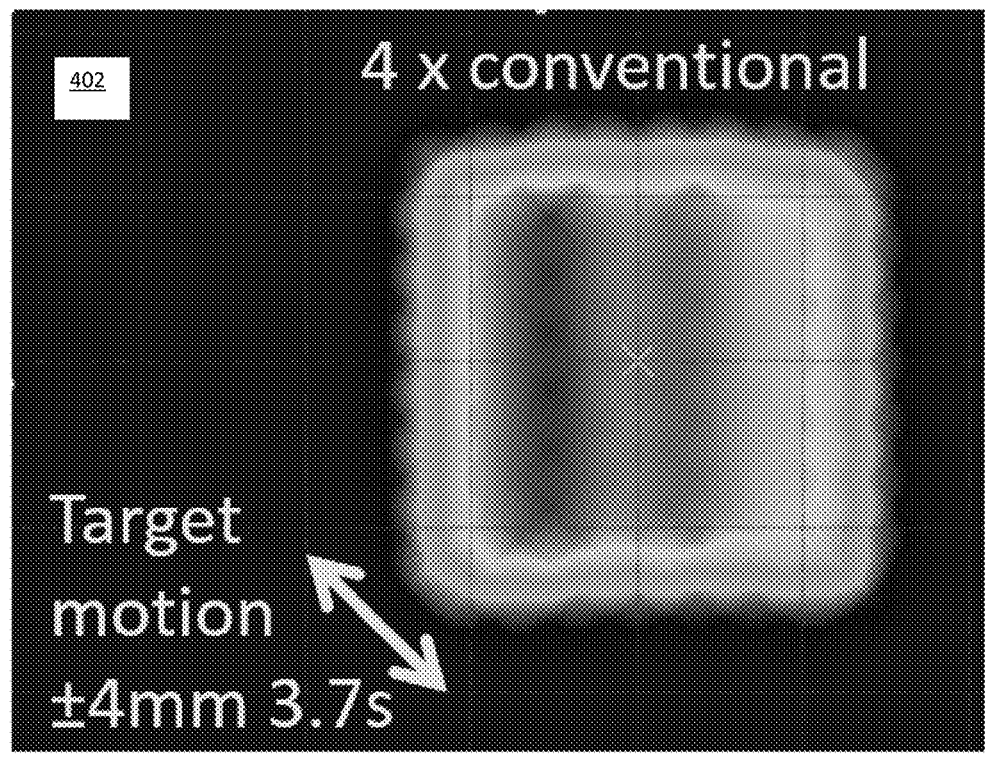
FIG. 4B illustrates an absolute dose measurement of an exemplary conventional repainting application for a target in motion.

With regard to FIGS. 4A and 4B, exemplary absolute dose measurements 401 and 402 demonstrate that a higher pass rate for Gamma 3%/3 mm can be achieved (93.7% vs. 68.5%) with random repainting, making it more time-efficient for achieving the same plan quality. In other words, the random repainting technique uses less paint (application of irradiation) compared to the conventional approach. FIG. 4A illustrates an absolute dose measurement 401 of an exemplary 4× random repainting application with target motion ±4 mm and 3.7 s motion cycle according to embodiments of the present invention. FIG. 4B illustrates an absolute dose measurement 402 of a conventional repainting technique for target oblique shifts by ±4 mm and a 3.7 s motion cycle (without random repainting).

Figure 5A:
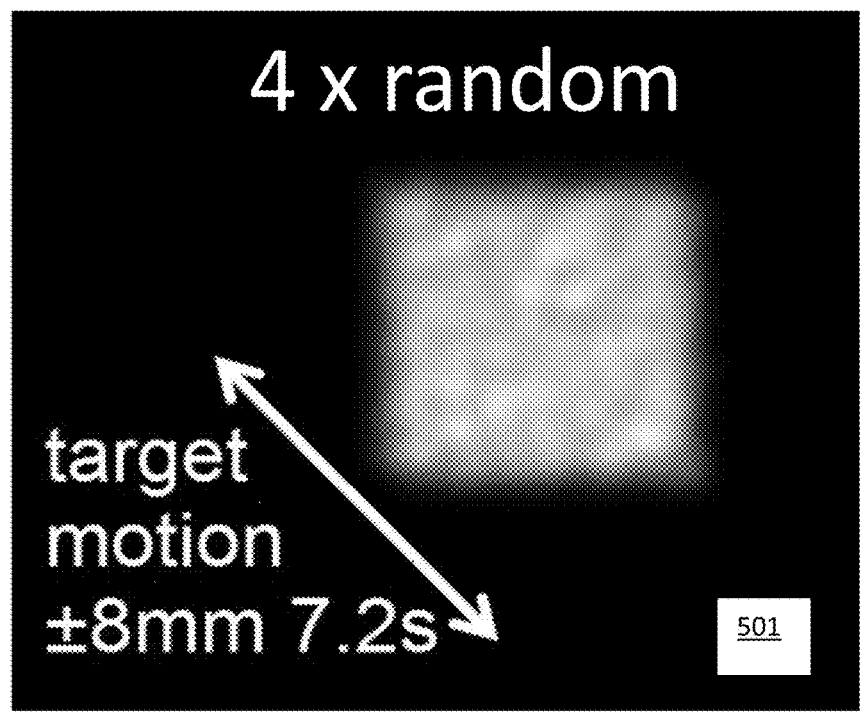
FIG. 5A illustrates an integrated dose distribution of a 4× random repaint according to embodiments of the present invention.
Figure 5B:
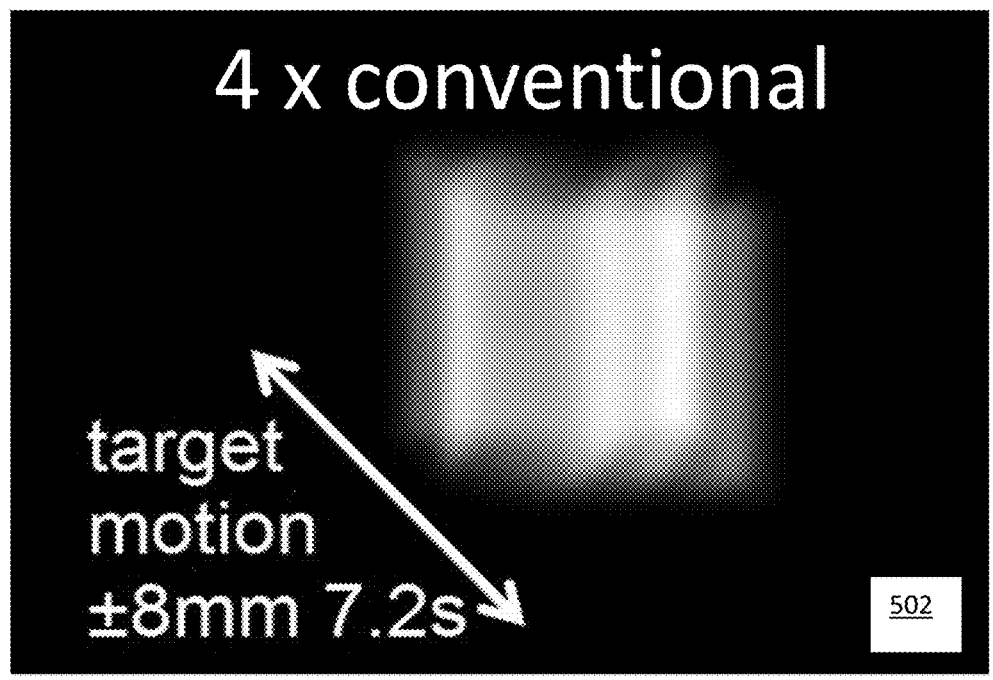
FIG. 5B illustrates an integrated dose distribution of a conventional repaint.

With regard to FIGS. 5A and 5B, exemplary integrated dose distributions for 4× random repainting applications with oblique shifts of ±8 mm and 7.2 s motion cycle are depicted according to embodiments of the present invention. FIG. 5A illustrates an integrated dose distribution 501 of a 4× random repaint with a potential motion amplitude pass rates of 82.8%. FIG. 5B illustrates an integrated dose distribution 502 of a conventional repaint (without random repainting).

Figure 6:
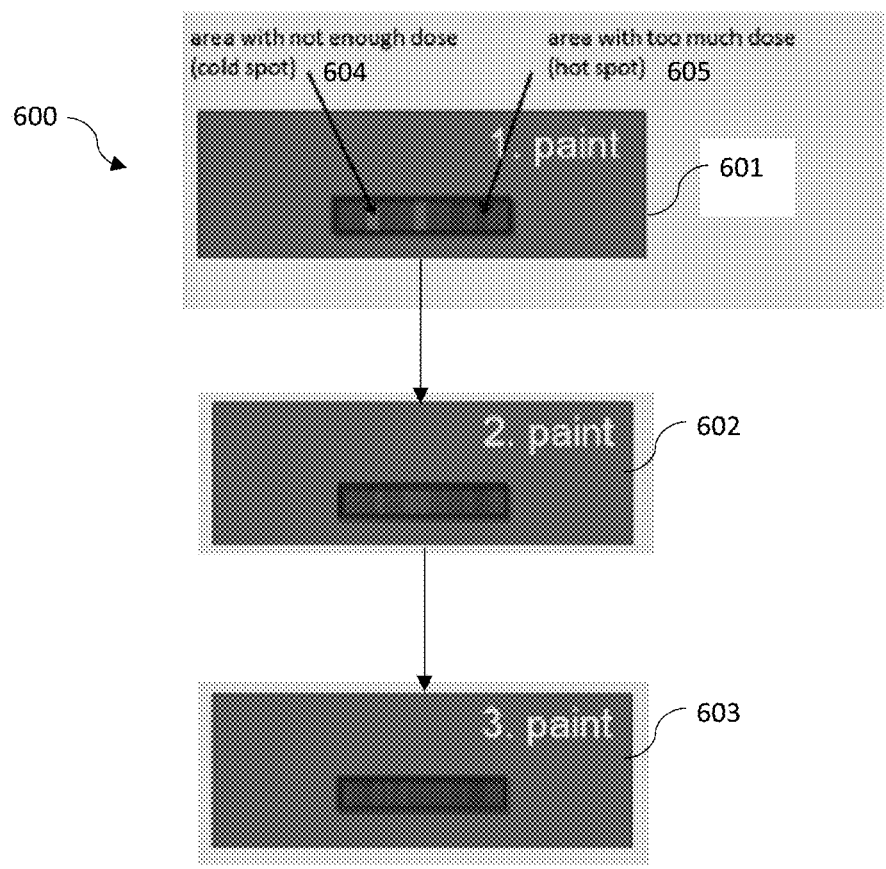
FIG. 6 illustrates a sequence of three paints of an exemplary random repaint process according to embodiments of the present invention.

With regard to FIG. 6, three paints (scans) 601-603 of an exemplary random repaint process 600 are depicted according to embodiments of the present invention. Subsequent to paint 601, areas with not enough dose 604 (cold spots) and areas with too much dose 605 (hot spots) are present in the target region. Subsequent to paint 602, the hot and cold spots have been blended together. The random paint process 600 ends subsequent to paint 603, and a uniform target dose distribution is achieved.

Figure 7:
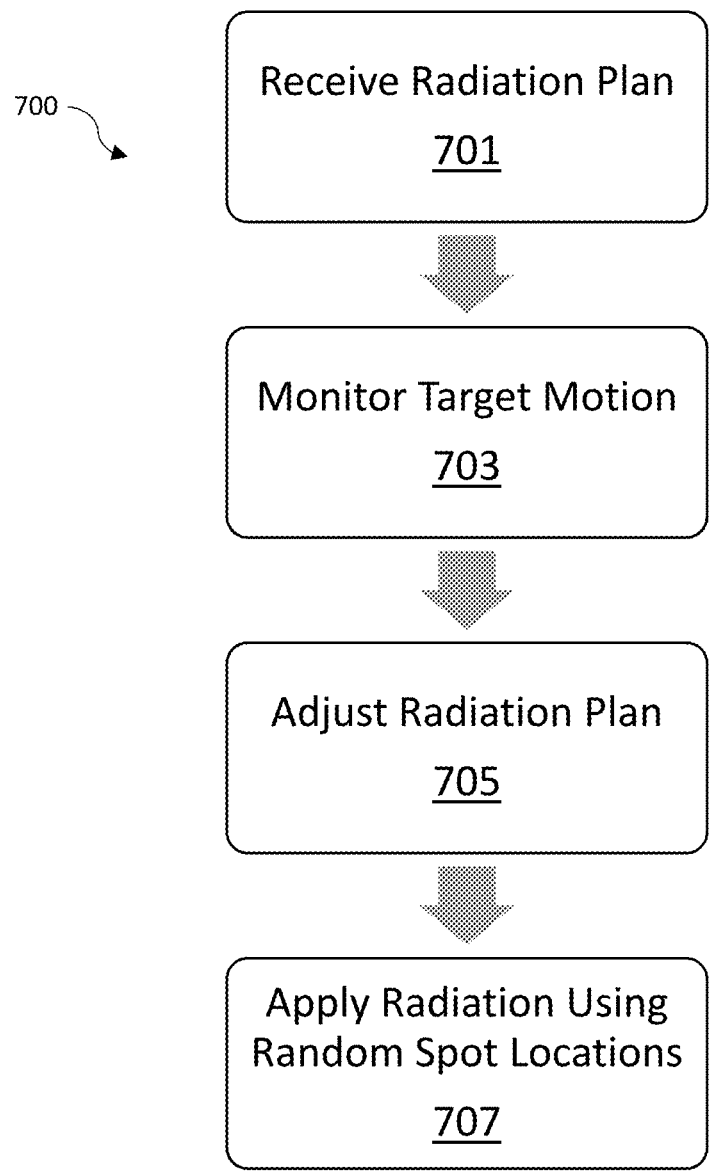
FIG. 7 is a flowchart depicting an exemplary sequence of steps for performing a random repaint application according to embodiments of the present invention.

With regard to FIG. 7, a flow chart depicting an exemplary sequence of steps for irradiating a target area with a proton beam using random repainting to achieve a uniform dose distribution and mitigate interplay effects is depicted according to embodiments of the present invention. Steps 701-707 describe exemplary steps comprising the process 700 depicted in FIG. 7 in accordance with the various embodiments herein described. In one embodiment, the process 700 is implemented in whole or in part as computer-executable instructions stored in a computer-readable medium and executed in a computing device.

At step 701, a radiation plan is received or accessed for a target area of a radiation subject. In one or more embodiments, the radiation plan may comprise a proton therapy plan for a patient undergoing radiation (proton-therapy) treatment. According to one or more embodiments, the radiation plan is received as data in a computing device executing an application operable to control a proton therapy treatment machine. The radiation plan may be pre-generated and associated with the radiation subject, and stored as one of a multitude of pre-generated records associated with a corresponding multitude of radiation subjects. According to some embodiments, the radiation plan includes a random pattern of locations used for random repainting. In still further embodiments, the radiation plan may be include a timing sequence and position data for applications of a random spot-scanning proton beam during a treatment session.

At step 703, a motion of the target area is monitored. Motion of the target area may be monitored by, but is not limited to, continuous imaging the target volume and/or tracking one or more motion surrogates directly correlated to the motion and/or position of a target volume. In one or more embodiments, the motion may be monitored indirectly by monitoring a displacement of an adjacent field or object. Motion data is tracked using the sensors, and characteristics of periodic motions (e.g., inhalation and exhalation, heartbeats) exhibited by the target area are measured. These characteristics may include, for example, a frequency of a periodic motion, the duration of each phase in the periodic motion, and the timing of any transition period between each phase.

At step 705, the radiation plan received in step 701 is dynamically adjusted to align the timing sequences and position data of the scanning application with the periodic motion exhibited by the target area measured in step 703. Adjusting the radiation plan may be accomplished by a variety of beam and periodic motion characteristics. For example, a starting position of an application of a spot-scanning beam can be aligned with a phase of periodic movement such as a respiratory motion by altering the start position of each scan to begin at an arbitrary position within the target area during each phase in the periodic motion. Other characteristics of the beam may be aligned with the motion of the target area. For example, the number of random spot scans or repaint applications may be increased or decreased by specifically mapping raster scans to phases.

In one or more embodiments, the beam applications may be gated around the periodic motion so that proton beam is not applied during or near transition periods or when the target area accelerates, or otherwise maximizes the application of the beam during periods of rest or constant motion. Gating around the periodic motion may be accomplished by adding artificial delays or pauses in the timing sequence of the radiation plan to delay application of the beam during transitions between phases, or even to pause applications during specific phases.

At step 707, the proton (e.g., spot-scanning) beam is applied according to the adjusted radiation plan determined at step 705. In one or more embodiments, the beam may be applied as a sequence of random spot scans for one or more layers in a target area. In one embodiment, the scanning direction of the beam application is aligned at step 705 to complement the direction of the motion of the target area. For example, a target area may extend laterally during exhalation and retract during inhalation. If an application requires more time than available (for example by a duty cycle at using beam gating), a deliberate pause may be added to the scan (e.g., a duration of a complete cycle of the periodic motion). Thus, irradiations with scanned particles can be resumed when the target area is at the same position in space when the scan was paused before.

In one or more embodiments, steps 703 through 707 may be performed in real-time, such that the adjustment of a radiation plan and the application of a proton therapy beam may be aligned dynamically with the detected motion of a target area.

According to some embodiments, the effectiveness of motion management is further improved using gating techniques.

According to some embodiments, potential effects of target are motion are mitigated using techniques such as rescanning by energy slice, rescanning of volume, repainting using random modulations, random delays between repaints, scaled rescanning, isolayered rescanning, beam tracking, etc.

According to some embodiments, the target is irradiated using random spot-scanning, where the spot size is variable and/or random. The treatment planning may consider motion interplay effects and use the variable and/or random spot size to achieve homogenous dose distribution while mitigating or curing the motion interplay.

Exemplary Computer System

Figure 8:
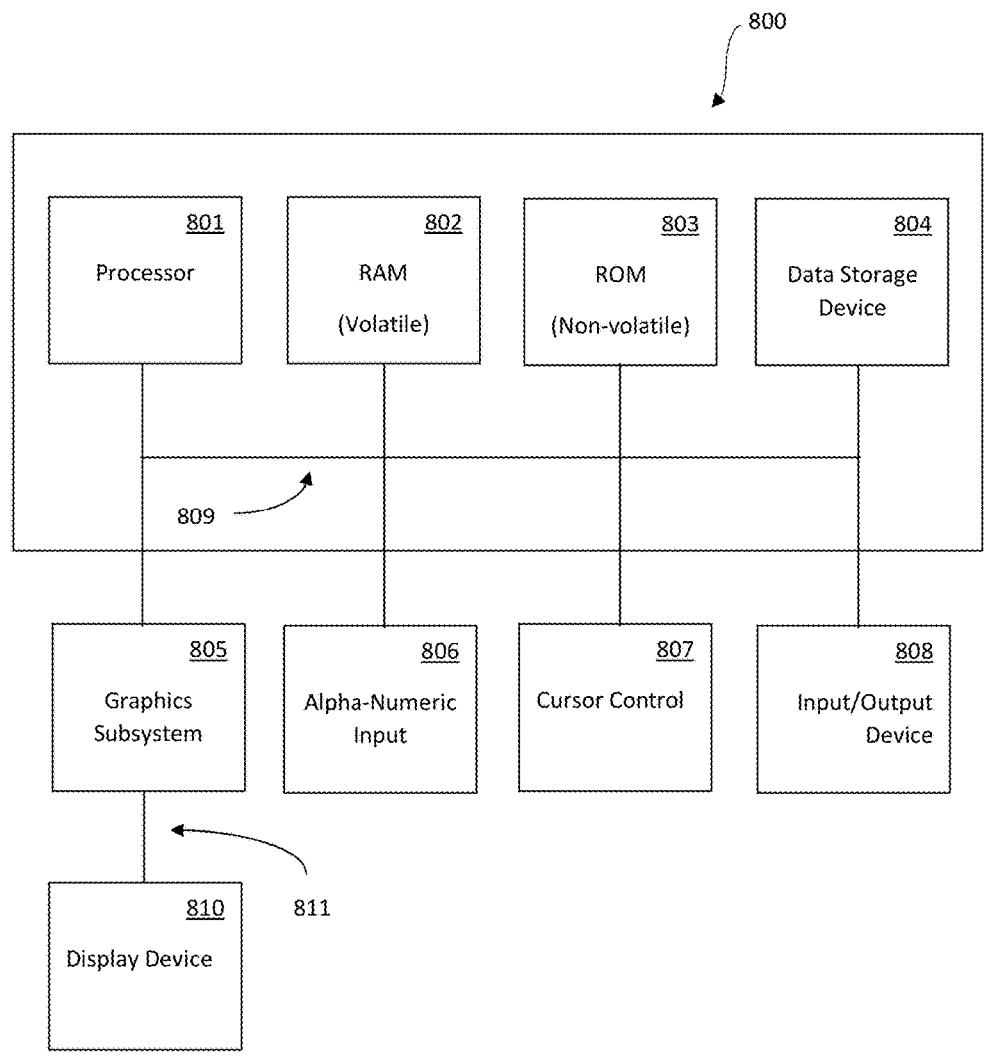
FIG. 8 depicts an exemplary computing environment, in accordance with embodiments of the present invention.

In one or more embodiments, alignment of the beam application with the motion of the target area may be executed as a series of programmed instructions executed on a computing environment operable to control the motion and emission of the radiation therapy machine described above with respect to FIG. 1. FIG. 8 depicts such a computing environment, including computing system 800 upon which embodiments of the present invention may be implemented includes a general purpose computing system environment. In its most basic configuration, computing system 800 typically includes at least one processing unit 801 and memory, and an address/data bus 809 (or other interface) for communicating information. Depending on the exact configuration and type of computing system environment, memory may be volatile (such as RAM 802), non-volatile (such as ROM 803, flash memory, etc.) or some combination of the two.

The computer system 800 may also comprise an optional graphics subsystem 805 for presenting information to the radiologist or other user, e.g., by displaying information on an attached display device 810, connected by a video cable 811. According to embodiments of the present claimed invention, the graphics subsystem 805 may be coupled directly to the display device 810 through the video cable 811. A graphical user interface of an application for grouping multiple beam fields may be generated in the graphics subsystem 805, for example, and displayed to the user in the display device 810. In alternate embodiments, display device 810 may be integrated into the computing system (e.g., a laptop or netbook display panel) and will not require a video cable 811.

Additionally, computing system 800 may also have additional features/functionality. For example, computing system 800 may also include additional storage (removable and/or non-removable) including, but not limited to, magnetic or optical disks or tape. Computer storage media includes volatile and nonvolatile, removable and non-removable media implemented in any method or technology for storage of information such as computer readable instructions, data structures, program modules or other data. RAM 802, ROM 803, and external data storage device (not shown) are all examples of computer storage media.

Computer system 800 also comprises an optional alphanumeric input device 806, an optional cursor control or directing device 807, and one or more signal communication interfaces (input/output devices, e.g., a network interface card) 808. Optional alphanumeric input device 806 can communicate information and command selections to central processor 801. Optional cursor control or directing device 807 is coupled to bus 809 for communicating user input information and command selections to central processor 801. Signal communication interface (input/output device) 808, also coupled to bus 809, can be a serial port. Communication interface 808 may also include wireless communication mechanisms. Using communication interface 808, computer system 800 can be communicatively coupled to other computer systems over a communication network such as the Internet or an intranet (e.g., a local area network).

In one or more embodiments, computing system 800 may be located in the same treatment room or suite as the radiation therapy device 100 described above with respect to FIG. 1. Alternately, computing system 800 may also be located externally with respect to the treatment room or suite containing treatment device 800.

By utilizing the systems and methods described above, the application of irradiated particles (such as protons) can be directed with greater precision by aligning beam applications with the periodic motion of a target area through the dynamic adjustment of beam characteristics and parameters. This alignment—all of which can be performed within a single, computing system—can effectively reduce misdirected, under-radiated, or misapplied beam applications and provide a more optimized treatment or radiation plan for radiation subjects.

Although the subject matter has been described in language specific to structural features and/or processor logical acts, it is to be understood that the subject matter defined in the appended claims is not necessarily limited to the specific features or acts described above. Rather, the specific features and acts described above are disclosed as example forms of implementing the claims.

What is claimed is:

1. A method for irradiating a target area using randomly distributed spot locations, the method comprising:

accessing a target radiation plan, the target radiation plan comprising a temporal and spatial sequence for administering a target dosage to a target using a first plurality of applications of a directed beam of particles;

painting the target with the first plurality of applications of the directed beam of particles according to the target radiation plan; and subsequent to said painting, repainting a first pattern of spot locations of the target with a second plurality of applications of the directed beam of particles, wherein the first pattern of spot locations is selected at random.

2. The method according to claim 1, further comprising, subsequent to said repainting the first pattern of spot locations, repainting a second pattern of spot locations of the target with a third plurality of applications of the directed beam of particles, wherein the second pattern of spot locations is selected at random.

3. The method according to claim 2, wherein the directed beam of particles comprises a spot scanning proton beam, a first spot scanning sequence is selected at random for the first pattern of spot locations, a second spot scanning sequence is selected at random for the second pattern of spot locations, said repainting the first pattern of spot locations is performed using the first spot scanning sequence, and said repainting the second pattern of spot locations is performed using the second spot scanning sequence.

4. The method according to claim 3, wherein said repainting the first pattern of spot locations comprises applying a first fraction of the target dosage to each of the spot locations in the first pattern, and said repainting the second pattern of spot locations comprises applying a second fraction of the target dosage to each of the spot locations in the second pattern.

5. The method according to claim 2, wherein a first spot scanning sequence is selected for the first pattern of spot locations, a second spot scanning sequence is selected for the second pattern of spot locations, said repainting the first pattern of spot locations is performed using the first spot scanning sequence, and said repainting the second pattern of spot locations is performed using the second spot scanning sequence, and wherein the first and second spot scanning sequences are selected based on a criterion selected from the group consisting of: scanning efficiency; dose homogeneity; and a balance between scanning efficiency and dose homogeneity.

6. The method according to claim 1, further comprising monitoring movement of the target.

7. The method according to claim 1, further comprising, prior to said painting, aligning the first plurality of applications of the directed beam of particles with movement of the target.

8. The method according to claim 7, wherein the movement of the target comprises a plurality of phases of periodic movement delineated by a plurality of transition periods between the plurality of phases of periodic movement, wherein said aligning comprises an operation selected from the group consisting of:

aligning a starting position of an application of the directed beam of particles with a direction of a phase of periodic movement;

adjusting a number of random repainting scans for producing the target dose;

adjusting a number of randomly selected spot locations for producing the target dose;

adjusting a dose rate of an application of the directed beam of particles based on a phase of periodic movement; and gating applications of the directed beam of particles outside of the plurality of phases of periodic movement, wherein the directed beam of particles is not applied to the target during a transition period.

9. The method according to claim 7, wherein said aligning comprises inserting a plurality of pauses in the temporal sequence of the target radiation plan to align the first plurality of applications of the directed beam of particles with a frequency of the movement of the target.

10. The method according to claim 1, wherein the directed beam of particles is selected from the group consisting of: a proton beam; a neutron beam; and an ion beam.

11. A radiation application system, comprising:

a particle accelerator configured to produce a plurality of particles;

a gantry coupled to the particle accelerator and configured to rotate around a target;

a treatment nozzle coupled to the particle accelerator and configured to emit the plurality of particles as a directed beam at a target in the target; and a computing device coupled to the gantry and to the treatment nozzle and comprising:

a memory device configured to store a target radiation plan comprising a timed sequence for irradiating the target with a first plurality of applications of the directed beam of the particles; and a processor configured to access the target radiation plan, to control rotation of the gantry, and to control the treatment nozzle, to paint the target with the first plurality of applications of the directed beam of the particles according to the target radiation plan and, subsequent to painting the target with the first plurality of applications of the directed beam of the particle, to repaint a first pattern of spot locations of the target with a second plurality of applications of the directed beam of the particles, wherein the first pattern of spot locations is selected at random.

12. The system according to claim 11, wherein the directed beam of the particles comprises a spot scanning proton beam, a first spot scanning sequence is selected at random for the first pattern of spot locations, and repainting the first pattern of spot locations is performed using the first spot scanning sequence.

13. The system according to claim 11, wherein a first spot scanning sequence is selected for the first pattern of spot locations, repainting the first pattern of spot locations is performed using the first spot scanning sequence, wherein the first spot scanning sequence is selected based on a criterion selected from the group consisting of: scanning efficiency; dose homogeneity; and a balance between scanning efficiency and dose homogeneity.

14. A non-transitory computer readable medium comprising a plurality of programmed instructions that, when executed by a processor in a computing system, is operable to implement a target radiation plan using randomly distributed spot locations, the computer readable medium comprising:

instructions to access the target radiation plan, wherein the target radiation plan comprises a temporal and spatial sequence for administering a target dosage to a target using a first plurality of applications of a directed beam of particles;

instructions to paint the target with the first plurality of applications of the directed beam of particles according to the target radiation plan; and instructions to repaint, subsequent to painting the target with the first plurality of applications of the directed beam of particles, a first pattern of spot locations of the target with a second plurality of applications of the directed beam of particles, wherein the first pattern of spot locations is selected at random.

15. The computer readable medium according to claim 14, further comprising instructions to repaint, subsequent to repainting the first pattern of spot locations, a second pattern of spot locations of the target with a third plurality of applications of the directed beam of particles, wherein the second pattern of spot locations is selected at random.

16. The computer readable medium according to claim 15, wherein the directed beam of particles comprises a spot scanning proton beam, a first spot scanning sequence is selected at random for the first pattern of spot locations, a second spot scanning sequence is selected at random for the second pattern of spot locations;
- wherein said repainting the first pattern of spot locations is performed using the first spot scanning sequence, wherein repainting the second pattern of spot locations is performed using the second spot scanning sequence; and
- wherein said repainting the first pattern of spot locations comprises applying a first fraction of the target dosage to each of the spot locations in the first pattern, and wherein said repainting the second pattern of spot locations comprises applying a second fraction of the target dosage to each of the spot locations in the second pattern.

17. The computer readable medium according to claim 15, wherein a first spot scanning sequence is selected for the first pattern of spot locations, a second spot scanning sequence is selected for the second pattern of spot locations, wherein said repainting the first pattern of spot locations is performed using the first spot scanning sequence, wherein repainting the second pattern of spot locations is performed using the second spot scanning sequence, and wherein the first and second spot scanning sequences are selected based on a criterion selected from the group consisting of: scanning efficiency; dose homogeneity; and a balance between scanning efficiency and dose homogeneity.

18. The computer readable medium according to claim 14, further comprising instructions to align, prior to painting the target with the first plurality of applications of the directed beam of particles, the first plurality of applications of the directed beam of particles with movement of the target.

19. The computer readable medium according to claim 18, wherein the movement of the target comprises a plurality of phases of periodic movement delineated by a plurality of transition periods between the plurality of phases of periodic movement, wherein aligning the first plurality of applications of the directed beam of particles with movement of the target comprises an operation selected from the group consisting of:
- aligning a starting position of an application of the directed beam of particles with a direction of a phase of periodic movement;
- adjusting a number of random repainting scans for producing the target dose;
- adjusting a number of randomly selected spot locations for producing the target dose;
- adjusting a dose rate of an application of the directed beam of particles based on a phase of periodic movement; and
- gating applications of the directed beam of particles outside of the plurality of phases of periodic movement, wherein the directed beam of particles is not applied to the target during a transition period.

20. The computer readable medium according to claim 18, wherein aligning the first plurality of applications of the directed beam of particles with movement of the target comprises inserting a plurality of pauses in the temporal sequence of the target radiation plan to align the first plurality of applications of the directed beam of particles with a frequency of the movement of the target.

* * * * *